United States Patent
Detsky et al.

(10) Patent No.: US 9,395,431 B2
(45) Date of Patent: Jul. 19, 2016

(54) MULTI-CONTRAST DELAYED ENHANCEMENT CARDIAC MAGNETIC RESONANCE IMAGING

(75) Inventors: Jay S. Detsky, North York (CA); Graham A. Wright, Toronto (CA)

(73) Assignee: SUNNYBROOK HEALTH SCIENCES CENTER, Ontario (CA)

( * ) Notice: Subject to any disclaimer, the term of this patent is extended or adjusted under 35 U.S.C. 154(b) by 2418 days.

(21) Appl. No.: 12/113,675

(22) Filed: May 1, 2008

(65) Prior Publication Data
US 2009/0275822 A1    Nov. 5, 2009

(51) Int. Cl.
| | |
|---|---|
| A61B 5/055 | (2006.01) |
| G01R 33/563 | (2006.01) |
| A61B 5/00 | (2006.01) |
| G01R 33/50 | (2006.01) |
| G01R 33/56 | (2006.01) |
| G01R 33/561 | (2006.01) |
| G01R 33/567 | (2006.01) |
| G01R 33/565 | (2006.01) |

(52) U.S. Cl.
CPC .......... G01R 33/56325 (2013.01); A61B 5/055 (2013.01); A61B 5/7285 (2013.01); G01R 33/50 (2013.01); G01R 33/5601 (2013.01); G01R 33/5614 (2013.01); G01R 33/5673 (2013.01); *G01R 33/5602* (2013.01); *G01R 33/56509* (2013.01)

(58) Field of Classification Search
None
See application file for complete search history.

(56) References Cited

U.S. PATENT DOCUMENTS

| | | | |
|---|---|---|---|
| 6,292,683 B1 | 9/2001 | Gupta et al. | |
| 6,781,375 B2 * | 8/2004 | Miyazaki et al. | 324/314 |
| 2005/0065430 A1 * | 3/2005 | Wiethoff et al. | 600/413 |
| 2005/0196027 A1 | 9/2005 | O'Donnell et al. | |
| 2005/0245809 A1 * | 11/2005 | Wolff et al. | 600/410 |
| 2005/0245812 A1 * | 11/2005 | Kim et al. | 600/410 |
| 2006/0161060 A1 * | 7/2006 | Pai | 600/431 |
| 2007/0135705 A1 * | 6/2007 | Lorenz et al. | 600/410 |
| 2008/0242973 A1 * | 10/2008 | Warmuth | 600/413 |

OTHER PUBLICATIONS

Gustafson et al, "Fuzzy Clustering With a Fuzzy Covariance Matrix", 1978 IEEE Conference on Decision and Control Including the 17th Symposium on Adaptive Processes, 1978, pp. 761-766.*
Markl M, et al., "Flow effects in balanced steady state free precession imaging," Magn Reson Med 2003; 50:892-903.
Guttman Ma, et al., "Imaging of myocardial infarction for diagnosis and intervention using real-time interactive MRI without ECG-gating or breath-holding," Magn Reson Med 2004; 52:354-361.
Schmitt P, et al., "Inversion recovery TrueFISP: quantification of T1, T2 and spin density," Magn Reson Med 2004; 51: 661-667.

(Continued)

*Primary Examiner* — Long V Le
*Assistant Examiner* — Bradley Impink
(74) *Attorney, Agent, or Firm* — Quarles & Brady, LLP

(57) ABSTRACT

A series of MR image frames are acquired that depict a subject's heart at successive cardiac phases. Delayed enhancement of infarcted myocardium is depicted in some of the image frames by administering a contrast agent prior to data acquisition. Data acquisition is performed in a single breath hold by producing an RF inversion pulse followed by segments of SSFP pulse sequences during a succession of cardiac gated heart beats. The acquired MR image frames depict contrast between blood, viable myocardium and non-viable myocardium, and they depict left ventricle wall thickness and wall thickening throughout the cardiac cycle.

17 Claims, 7 Drawing Sheets

(56) References Cited

OTHER PUBLICATIONS

Sharma P, et al., "Post-contrast T1 measurements of blood, infarct and normal myocardium at 1.5T and 3T," Proc Intl Soc Magn Res Med 2005; 13:235.

Schmidt A, et al., "Infarct tissue heterogeneity by magnetic resonance imaging identifies enhanced cardiac arrhythmia susceptibility in patients with left ventricular dysfunction," Circ 2007; 115:2006-2014.

* cited by examiner

MULTI-CONTRAST DELAYED ENHANCEMENT CARDIAC MAGNETIC RESONANCE IMAGING

BACKGROUND OF THE INVENTION

The field of the invention is magnetic resonance imaging ("MRI") methods and systems. More particularly, the invention relates to delayed enhancement cardiac MRI.

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

The MR signals acquired with an MRI system are signal samples of the subject of the examination in Fourier space, or what is often referred to in the art as "k-space". Each MR measurement cycle, or pulse sequence, typically samples a portion of k-space along a sampling trajectory characteristic of that pulse sequence. Most pulse sequences sample k-space in a roster scan-like pattern sometimes referred to as a "spin-warp", a "Fourier", a "rectilinear" or a "Cartesian" scan. The spin-warp scan technique is discussed in an article entitled "Spin-Warp MR Imaging and Applications to Human Whole-Body Imaging" by W. A. Edelstein et al., Physics in Medicine and Biology, Vol. 25, pp. 751-756 (1980). It employs a variable amplitude phase encoding magnetic field gradient pulse prior to the acquisition of MR spin-echo signals to phase encode spatial information in the direction of this gradient. In a two-dimensional implementation (2DFT), for example, spatial information is encoded in one direction by applying a phase encoding gradient ($G_y$) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($\Delta G_y$) in the sequence of measurement cycles, or "views" that are acquired during the scan to produce a set of k-space MR data from which an entire image can be reconstructed.

There are many other k-space sampling patterns used by MRI systems These include "radial", or "projection reconstruction" scans in which k-space is sampled as a set of radial sampling trajectories extending from the center of k-space as described, for example, in U.S. Pat. No. 6,954,067. The pulse sequences for a radial scan are characterized by the lack of a phase encoding gradient and the presence of a readout gradient that changes direction from one pulse sequence view to the next. There are also many k-space sampling methods that are closely related to the radial scan and that sample along a curved k-space sampling trajectory rather than the straight line radial trajectory. Such pulse sequences are described, for example, in "Fast Three Dimensional Sodium Imaging", MRM, 37:706-715, 1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Magn. Reson. Med. 13 (2005) by J. G. Pipe and Koladia.

An image is reconstructed from the acquired k-space data by transforming the k-space data set to an image space data set. There are many different methods for performing this task and the method used is often determined by the technique used to acquire the k-space data. With a Cartesian grid of k-space data that results from a 2D or 3D spin-warp acquisition, for example, the most common reconstruction method used is an inverse Fourier transformation ("2DFT" or "3DFT") along each of the 2 or 3 axes of the data set. With a radial k-space data set and its variations, the most common reconstruction method includes "regridding" the k-space samples to create a Cartesian grid of k-space samples and then perform a 2DFT or 3DFT on the regridded k-space data set. In the alternative, a radial k-space data set can also be transformed to Radon space by performing a 1 DFT of each radial projection view and then transforming the Radon space data set to image space by performing a filtered backprojection.

Because it requires time to acquire a complete k-space MR data set, subject motion presents a problem in many clinical applications. Motion due to respiration and cardiac motion can produce image artifacts such as blurring or ghosting. There are many strategies used to suppress such artifacts. These include cardiac or respiratory gating techniques that acquire MR data only during certain phases of the cardiac or respiratory cycle. In gated cardiac MRI, for example, one or more k-space views of the heart ("segment") are acquired a preset time interval after the ECG triggered gating signal is produced. View segments for the image are acquired over a plurality of heart beats at the same preset time interval until sufficient data is acquired to reconstruct an image depicting the heart at that particular cardiac phase. By acquiring 8 to 16 views in each segment, a complete image can be acquired in one breath hold, thus eliminating respiratory motion issues. Typically, during a segmented cardiac MRI scan, segments of data will be acquired at a succession of cardiac phases during each cardiac cycle, or R-R interval, so that a plurality of images may be reconstructed at the conclusion of the scan which depict the heart at a corresponding succession of cardiac phases.

Delayed enhancement (DE) magnetic resonance imaging (MRI) is a cardiac MRI method for myocardial viability imaging. This method distinguishes healthy and infarcted myocardium. The identification of viable myocardium is useful for predicting which patients will have improved left ventricular (LV) ejection fractions and improved survival after revascularization. The transmural extent of infarcted tissue as determined by DE MRI has been shown to predict functional recovery post-revascularization procedures such as coronary bypass surgery.

DE MRI involves the injection of a bolus of a Gadolinium-based contrast agent called Gd-DTPA. Starting approximately ten minutes after the injection, Gd-DTPA preferentially pools in the areas of infarct due to differences in the wash-in times and distribution volumes between viable and non-viable tissue. The presence of a larger concentration of Gd-DTPA causes $T_1$ shortening in infarcted tissue. The standard MRI pulse sequence for visualizing these infarcts is an inversion recovery gradient echo (IR-GRE) pulse sequence which takes advantage of the short $T_1$ time of infarcted tissue to create images where viable tissue is nulled (dark) while infarcted tissue appears bright. A limitation of IR-GRE imaging for DE MRI is that blood in the left ventricle also appears bright. This makes it difficult to determine the border between blood and infarcted tissue and it can also result in the failure to detect small subendocardial infarcts that appear to be LV blood.

Cine imaging of the beating heart with MRI is performed during cardiac studies to visualize the wall thickness and systolic wall thickening throughout the cardiac cycle. With cine imaging complete k-space image data sets are acquired at a succession of cardiac phases so that the myocardium can be imaged throughout a complete cardiac cycle. Cine imaging is typically acquired with very short TR steady-state free precession (SSFP) imaging pulse sequences. These cine images are used to detect dysfunctional myocardium that may appear viable on DE MRI images. Cine imaging is also used to determine the LV ejection fraction to determine the overall pumping capacity of the heart.

DE MRI and cine images are acquired in a short axis view of the heart, and 10-15 slices are acquired during each scan to cover the entire left ventricle. Imaging a single anatomical slice for DE MRI or cine imaging requires a 10-20 second breath-hold. Currently, DE MRI and cine imaging are acquired separately, thus resulting in 20-30 of these breath holds. This can be quite difficult for some patients, and results in long scan times.

A real-time method for DE MRI imaging is disclosed by Guttman M A, Dick A J, Raman V K, et al. "Imaging of myocardial infarction for diagnosis and intervention using real-time interactive MRI without ECG-gating or breath-holding", *Magn Reson Med* 2004; 42:354-61, to alleviate the requirements of breath-holding and cardiac gating. However, this real-time method has a lower spatial resolution than conventional DE MRI, and the temporal resolution of 2-6 frames per second is not adequate for analyzing wall motion, thus still necessitating a separate cardiac cine scan. A cardiac-gated cine delayed enhancement pulse sequence for acquiring viability and wall motion images simultaneously is disclosed in published U.S. Patent Application No. 20050245812 filed on Nov. 3, 2005 and entitled "Acquiring Contrast-Enhanced, $T_1$-Weighted, Cine Magnetic Resonance Images". This method uses a single-shot acquisition over approximately 300 ms instead of a segmented acquisition, and thus blurring is introduced into the images, particularly during systole. This method also maintains the same tissue contrast throughout the cine images.

SUMMARY OF THE INVENTION

The present invention is a method for acquiring MR imaging data from a beating heart which enables the segmentation of healthy myocardium, infarcted myocardium and blood in reconstructed images and enables the visualization of wall motion and wall thickening over the cardiac cycle which enables calculation of ejection fractions. The entire scan is performed in a single breath hold.

The method includes performing a DE MRI scan in which a pulse sequence is used with an MRI system in which an inversion pulse is produced following a cardiac gating signal and a succession of steady-state free precession (SSFP) pulse sequence segments are produced throughout the remainder of each cardiac cycle. Image frames are reconstructed from the k-space data acquired during each segment, and the resulting successive image frames have different tissue contrast. Infarcted myocardium tissues is visualized in early segments in which blood and/or healthy myocardium tissues is suppressed and all the reconstructed image frames enable visualization of cardiac wall motion.

A general object of the invention is to acquire both myocardium viability images and wall motion information with a single pulse sequence. Twenty image frames may be produced from a single scan and the required tissue contrast information and wall motion information may be extracted from these. In addition, the succession of image frames enable the $T_1$ recovery curve to be calculated at each pixel location. This information may be employed to produce a $T_1$ map and a steady state signal value (ss) map that in turn may be used to more accurately segment tissue types in the image frames.

GENERAL DESCRIPTION OF THE INVENTION

Figure 1:
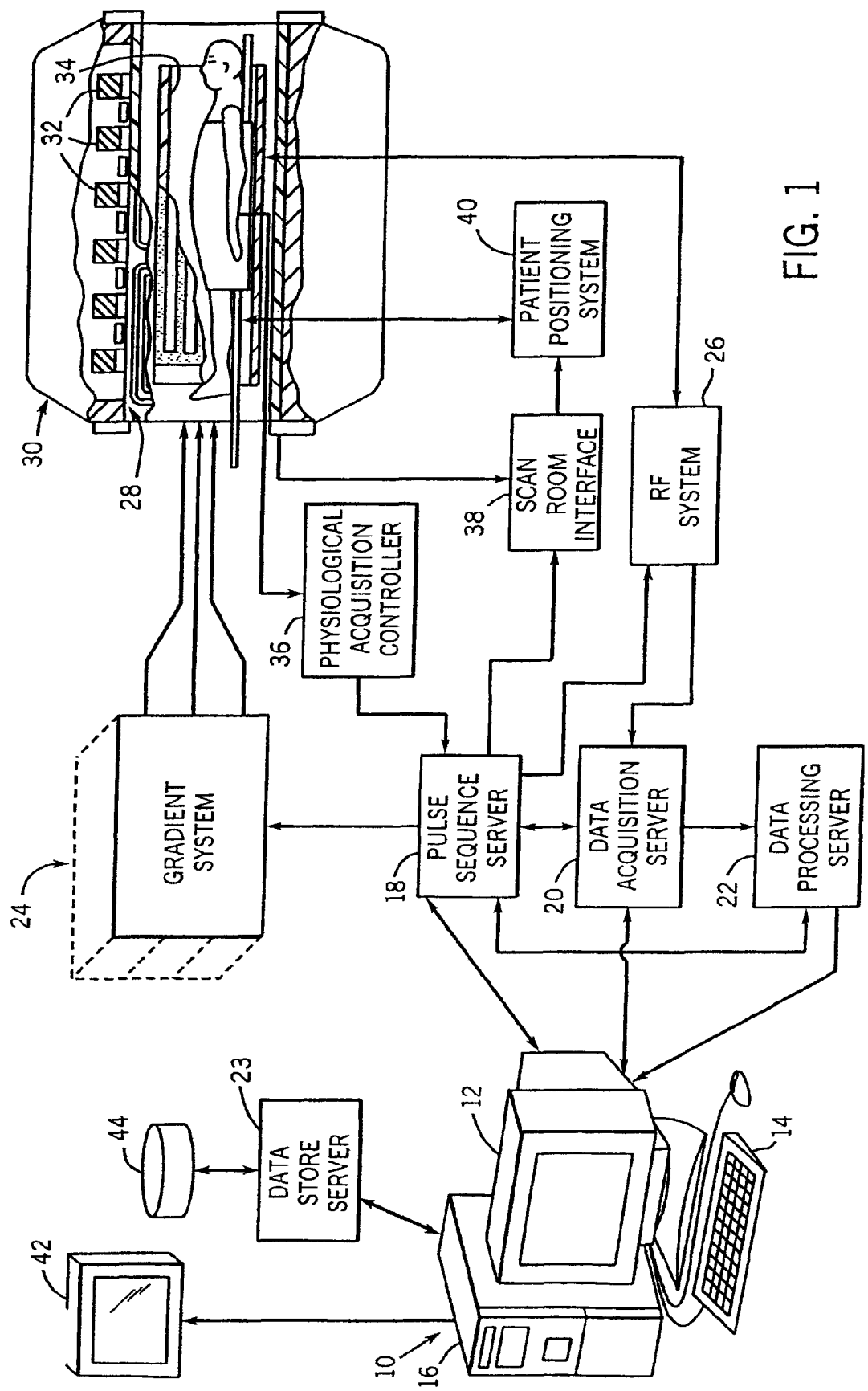
FIG. 1 is a block diagram of an MRI system that employs the present invention.

An important aspect of the present invention is the discovery that SSFP pulse sequences may be employed in an inversion recovery acquisition to acquire a succession of image frames that depict different tissue contrasts. We have discovered that the effects of an SSFP readout on magnetization behavior after an IR pulse in the setting of DE MRI can predictably produce the desired tissue contrasts. In particular, the effects of varying the SSFP flip angle are examined. We present a segmented, cardiac-gated IR-SSFP sequence with optimized parameters for infarct visualization. The goal of this sequence is to also provide cine images of the heart with varying contrast in order to simultaneously visualize myocardial wall motion and detect infarcted tissue.

The SSFP pulse sequence uses a train of ±α pulses with fully balanced gradient moments. With conventional SSFP imaging, a pulses are applied without any magnetization preparation, and after a number of pulses a steady-state signal is achieved that is $T_2/T_1$-weighted. For IR-SSFP, an SSFP readout is used during IR, and thus the magnetization is sampled during the transition from $T_1$ recovery to its true steady-state magnetization value. The evolution of the magnetization during an SSFP readout can be calculated using the recursive equation:

$$M_n = R_x(\pm\alpha)[E_2(TR, T_1, T_2)M_{n-1} + E_1(TR, T_1)] \quad [1]$$

where $M_n$ is the magnetization vector $[M_x\ M_y\ M_z]^T$ directly after the nth pulse and $Rx(\pm\alpha)$ is a rotation matrix about the x-axis in the rotating frame corresponding to an RF excitation with flip angle α. $E_1$ and $E_2$ are matrix representations of $T_1$ relaxation and $T_2$ decay, respectively:

$$E_1(TR, T_1) = [0\ \ 0\ \ M_0(1 - e^{-TR/T1})]^T \quad [2]$$

$$E_2(TR, T_1, T_2) = \begin{bmatrix} e^{-TR/T_2} & 0 & 0 \\ 0 & e^{-TR/T_2} & 0 \\ 0 & 0 & e^{-TR/T_2} \end{bmatrix}$$

Note that this formulation neglects off-resonance effects. An inversion pulse can be added between any two pulses via $$M_{inv} = R_x(\pi)M_n \quad [3]$$

where $M_{inv}$ is the magnetization vector directly after the inversion pulse, and $R_x(\pi)$ is the rotation matrix about the x-axis for a 180 degree inversion pulse.

Simulations were used to model the signal behavior of blood, healthy myocardium, and infarcted myocardium undergoing IR-SSFP for DE imaging. Immediately after the inversion pulse, six linearly ramped dummy pulses from α/6 to a were applied to minimize signal oscillations, followed by ±α SSFP readout pulses. The simulations used a TR of 3.4 ms. The inversion pulse is assumed to be non-slice-selective, meaning that blood entering the imaging slice after the inversion pulse will still follow an IR behavior. An ejection fraction (EF) of 60% is assumed in the simulations, meaning that after systole 60% of the blood pool is replaced by blood that has not been exposed to any prior SSFP pulses. The $T_1$ and $T_2$ values of the different tissues used in the simulations were obtained from previously published reports for a 1.5 T magnet, assuming a 10-min delay between Gd-DTPA injection and imaging. The parameters used were $T_{1,myo}$380 ms, $T_{2,myo}$=45 ms, $T_{1,inf}$=280 ms, $T_{2,inf}$=40 ms, $T_{1,blood}$=260 ms, and $T_{2,blood}$=180 ms.

Figure 3:
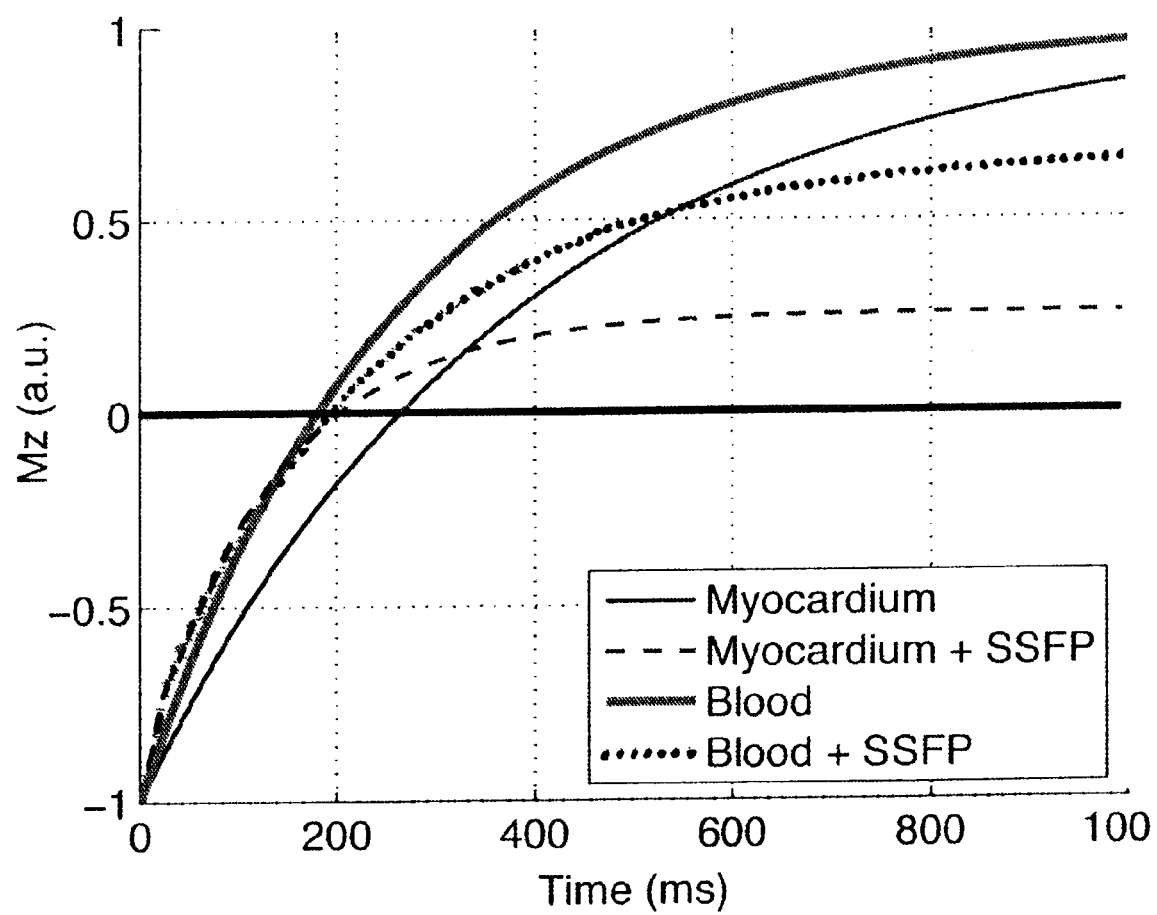
FIG. 3 is a graphic representation of a $T_1$ recovery of myocardium and blood after an RF inversion pulse.

FIG. 3 shows a comparison between the natural $T_1$ recovery of blood and myocardium and the actual recovery when undergoing IR-SSFP imaging with α=60 degrees. The signal behavior with an SSFP readout follows an exponential recovery with a time constant $T_1^*$ that is shorter than the true $T_1$. The $T_1^*$ shortening effect is more pronounced for myocardium and infarct ($T_2/T_1 \approx 0.1$) than for blood ($T_2/T_1 \approx 0.7$), and varies with the SSFP flip angle. The $T_1^*$ effect alters the dynamics between the three tissues of interest during IR-SSFP imaging compared to IR-GRE imaging.

Figure 4A:
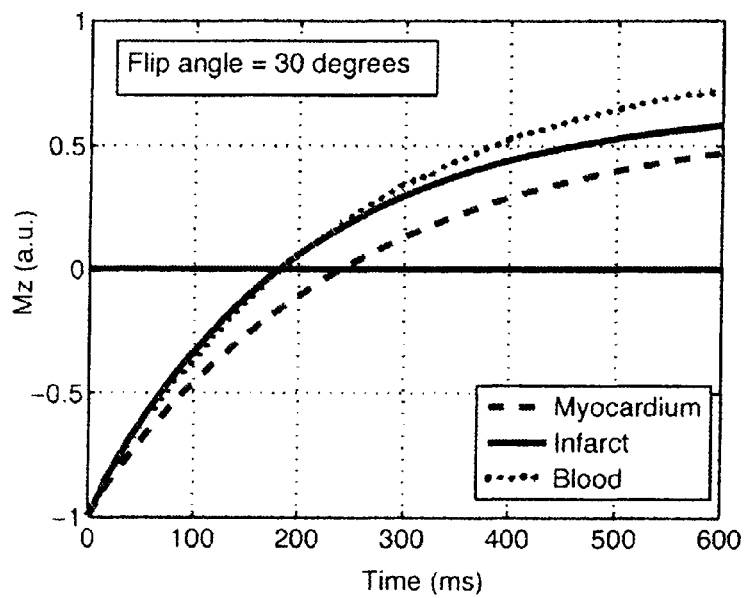
FIGS. 4A and 4B are magnetization recovery curves during a single-shot IR-SSFP acquisition pulse sequence using an RF excitation pulse flip angle of $\alpha=30$ degrees and $\alpha=60$ degrees respectively.
Figure 4B:
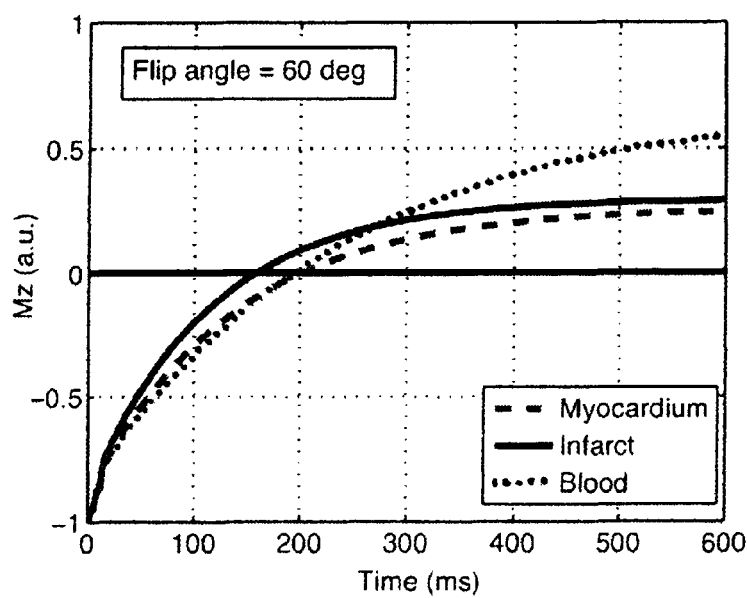

One method which may be used is a single-shot IR-SSFP sequence in which all phase-encoding lines for a single image are acquired within one heartbeat. The effects of changing the SSFP flip angle in the context of a single-shot IR-SSFP sequence are shown in FIG. 4. With a 30 degree flip angle, the simulations show that at TI=240 ms, normal myocardium will have no signal, while infarcted tissue and blood will have the same level of signal ($M_{z,inf}=M_{z,blood}$=0.17). This agrees with what has been seen experimentally. However, for a α=60 degrees, the myocardium is nulled earlier (at TI=200 ms), at which point the infarct has a small positive signal ($M_{z,inf}$=0.095) but blood has no signal ($M_{z,blood} \approx 0$). This means that with α=60 degrees, a black-blood appearance is achieved, but the contrast between healthy myocardium and infarct is reduced by 44%. Thus, in the setting of DE-MRI, an SSFP readout affects the optimal TI and image characteristics.

Figure 5A:
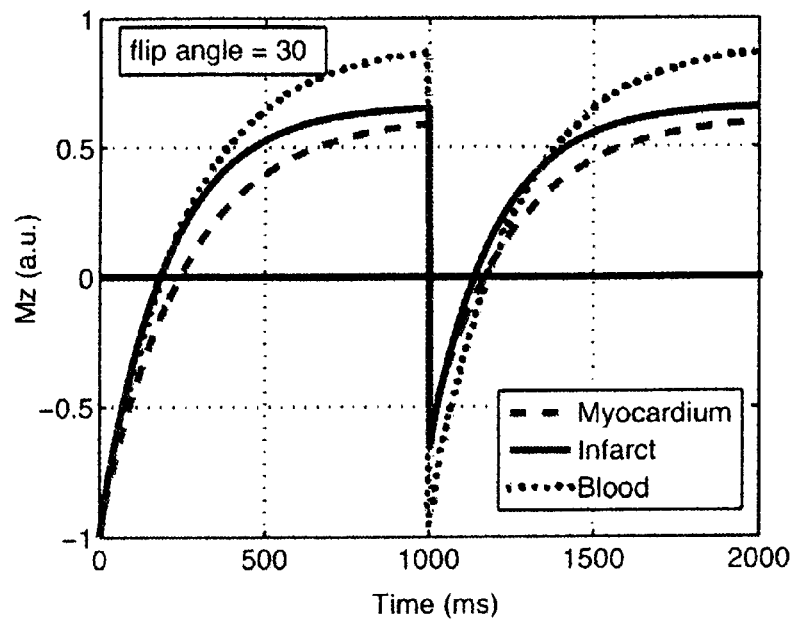
FIGS. 5A and 5B are magnetization recovery curves after the first two RF inversion pulses during a segmented IR-SSFP acquisition using the pulse sequence of FIG. 2 using an RF excitation pulse flip angle of $\alpha=30$ degrees and $\alpha=60$ degrees respectively.
Figure 5B:
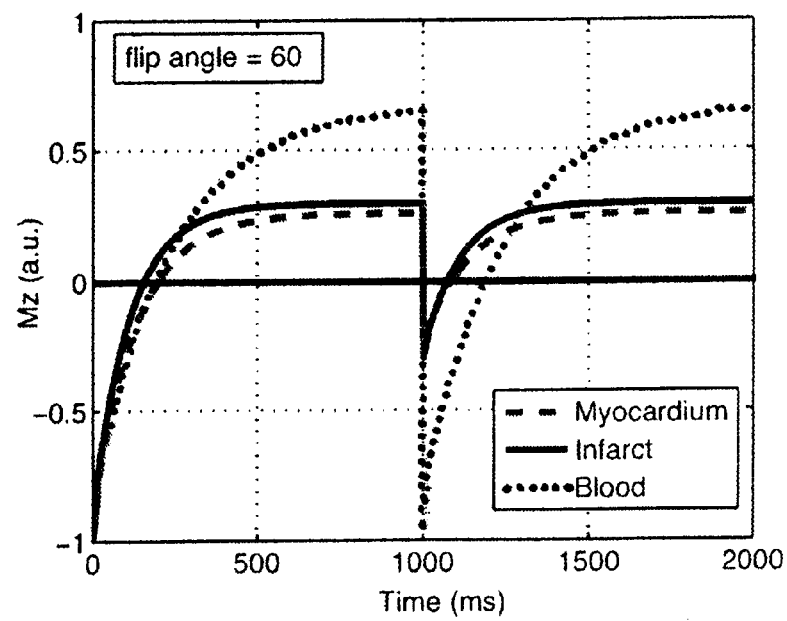

A difficulty with the single-shot technique is that blurring is introduced due to cardiac motion over the 250-400 ms required for a single acquisition. Simulations were therefore also performed to examine the signal behavior of IR-SSFP during a segmented DE-MRI sequence. A segmented approach acquires data during a small time window during each cardiac cycle; therefore, multiple inversion pulses (one per heartbeat, followed by an SSFP readout) are used to form a single image. After the first inversion pulse, the signal behavior would follow that of the single-shot IR-SSFP sequence (FIG. 4). The SSFP pulses, if played out continuously, would limit the regrowth of $M_z$ based on the SSFP flip angle and the $T_2/T_1$ ratio of a particular tissue. Thus, the magnetization values of myocardium, infarct, and the blood just prior to the second and all subsequent inversion pulses are not equal (FIG. 5). This alters the $M_z$ recovery curves of the three tissues relative to each other. FIG. 5 shows that for α=30 degrees, after the second inversion pulse, blood is nulled at approximately the same time point as myocardium. This suggests that an image acquired with these parameters would be a black-blood DE image. This has been seen experimentally with a real-time IR-SSFP sequence that uses α=30 degrees. FIG. 5 also shows that when α=60 degrees, blood has a large negative magnetization at the null point of myocardium. Blood would thus appear bright on a magnitude image acquired at that time point.

The simulations show that for any α, the $M_z$ recovery curves are consistent after the second and all subsequent inversion pulses. This holds true only if SSFP pulses are played out continuously between successive inversion pulses. It was observed that the IR behavior and dynamics did not change significantly with changes in the value of 60% used for the EF.

Figure 6A:
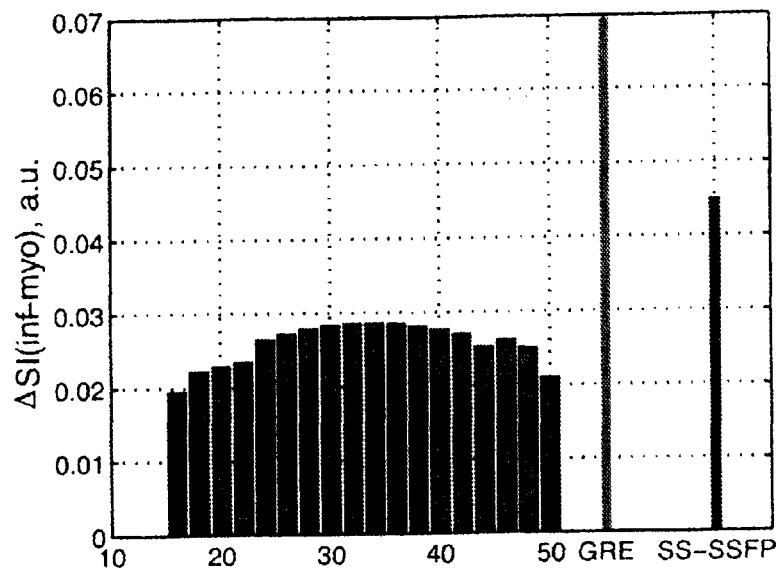
FIGS. 6A and 6B are graphic representations of the differences in signal intensity between infarcted myocardium and normal myocardium and the differences between infarcted myocardium and blood respectively.
Figure 6B:
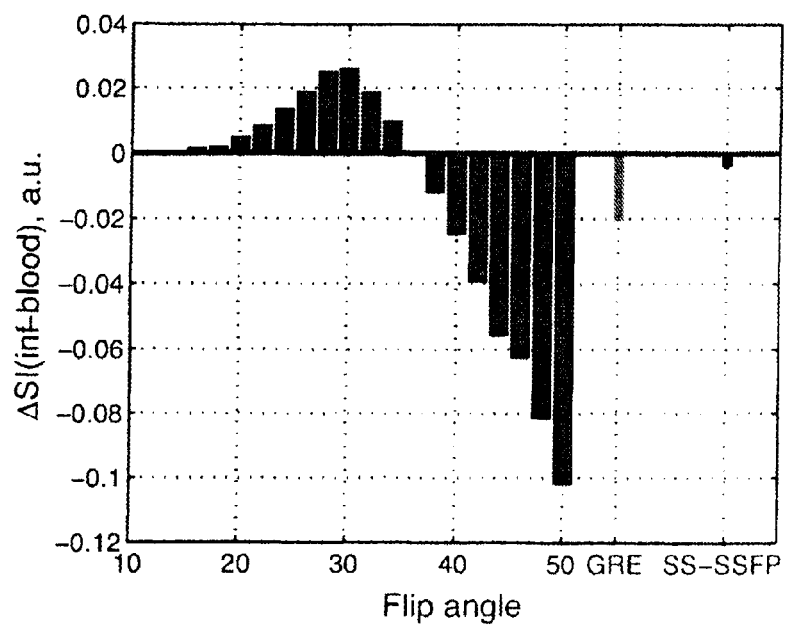

It is apparent from the simulations that the appearance of DE-MRI images will be affected by the readout scheme (GRE, single-shot SSFP, or segmented SSFP) and the readout flip angle. Further simulations were performed to determine the optimum flip angle for a segmented IR-SSFP sequence for visualizing infarcted tissue. The optimization examined the effect of various SSFP flip angles on the single intensity differences between infarct and myocardium ($\Delta SI_{inf-myo}$) and between infarct and blood ($\Delta SI_{inf-blood}$) at the time point where the signal from healthy myocardium is zero. The results were compared with simulated signal intensity differences for GRE and single-shot SSFP readouts (FIG. 6). The results indicate that for a segmented IR-SSFP scheme, α=30 degrees yields a maximum for both ($\Delta SI_{inf-myo}$) and ($\Delta SI_{inf-blood}$). These results are relatively insensitive to the TR of the SSFP pulses, with a range of TRs from 2.5 ms to 3.5 ms changing the optimum flip angle by only 2 degrees.

A 30 degree flip angle also produces recovery curves where blood and myocardium are nulled at the same time point (FIG. 5.), meaning that blood would have no signal in the corresponding DE-MRI image. For α=38 degrees and higher, and for a GRE and single-shot SSFP readout, $\Delta SI_{inf-blood}$ is negative, meaning that blood would appear brighter than infarct. This yields DE-MRI images that can be difficult to interpret because the boundary between infarct and blood is difficult to visualize. The cost of using a segmented IR-SSFP approach is that $\Delta SI_{inf\text{-}myo}$ is reduced by 56% compared to a GRE readout, and 36% compared to a single-shot SSFP readout. However, a segmented approach will have less blurring due to cardiac motion and the SNR can be boosted by averaging over multiple excitations. Furthermore, with a segmented approach, multiple images can be acquired over the cardiac cycle, as is done with cine SSFP cardiac imaging. One of the IR-SSFP images will be the equivalent of a conventional DE image (with nulled myocardium and bright infarct), while the other images can be used as a cine loop to visualize the motion of the heart. The IR-SSFP images have varying contrast because each image is acquired at a different effective TI. It is expected that visually tracking the $T_1$ recover of myocardium and infarct over all the IR-SSFP images will help compensate for the lower myocardium-to-infarct contrast in the myocardium-nulled IR-SSFP image.

DESCRIPTION OF THE PREFERRED EMBODIMENT

Referring particularly to FIG. 1, the preferred embodiment of the invention is employed in an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to four servers: a pulse sequence server 18; a data acquisition server 20; a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$, and $G_z$ used for position encoding MR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive MR signals detected by the RF coil 34 or a separate local coil (not shown in FIG. 1) are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays (not shown in FIG. 1).

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi = \tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during prescans MR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process MR signals used to detect the arrival of contrast agent in an MRA scan. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
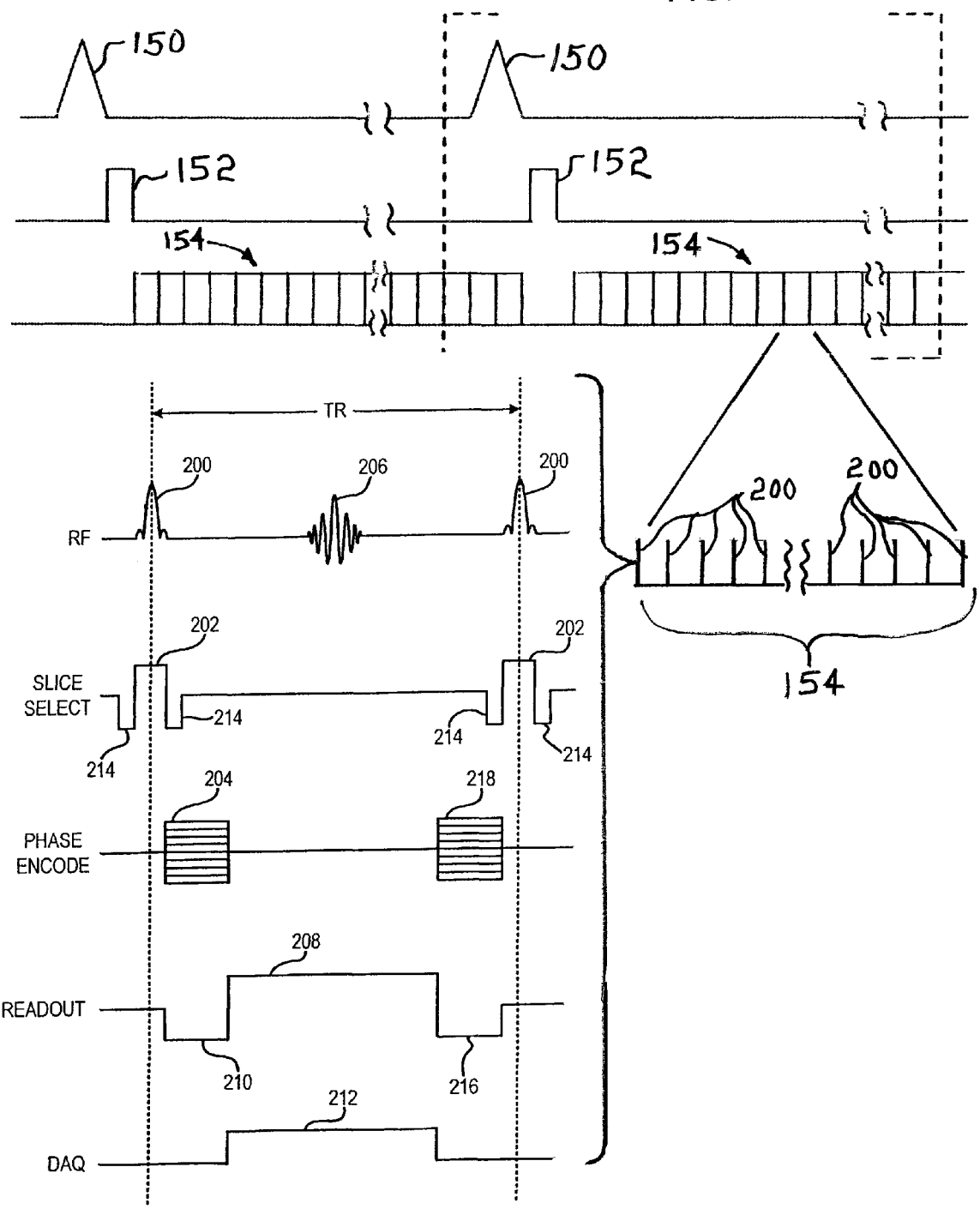
FIG. 2 is a graphic representation of a preferred embodiment of a pulse sequence used to acquire MR data with the MRI system of FIG. 1.

Referring particularly to FIG. 2, the present invention is a method for acquiring MR image data from a subject placed in the MRI system of FIG. 1 using a cardiac gated, inversion recovery segmented acquisition technique. A gating signal 150 is produced by the R wave of the ECG waveform to signal the start of each cardiac cycle. During the R-R interval between gating signals 150 a non-selective 180 degree RF inversion pulse 152 is produced to invert longitudinal spin magnetization throughout the heart. The R-R interval after the inversion pulse 152 is divided into a series of segments 154 that divide the cardiac cycle into a corresponding number of cardiac phases. During each segment 154 a plurality of SSFP MR pulses are performed to acquire a corresponding plurality of k-space views of the heart at the segment's cardiac phase.

A number of different SSFP pulse sequences can be used to direct the MRI system to acquire the data needed to practice the present invention. In the preferred embodiment a balanced SSFP pulse sequence is employed, such as the one shown in FIG. 2. It includes a selective RF excitation pulse 200 that is repeated at the start of each TR period as well as a slice select gradient pulse 202 that is produced concurrently with the RF pulse 200 to produce transverse magnetization in a prescribed slice. After excitation of the spins in the slice a phase encoding gradient pulse 204 is applied to position encode the MR signal 206 along one direction in the slice. A readout gradient pulse 208 is also applied after a dephasing gradient lobe 210 to position encode the MR signal 206 along a second, orthogonal direction in the slice. The MR signal 206 is sampled during a data acquisition window 212. To maintain the steady state condition, the integrals of the three gradients each sum to zero. To accomplish this, rephasing lobes 214 are added to the slice select gradient waveform, a rephasing lobe 216 is added to the readout gradient waveform 208 and a rewinder gradient lobe 218 is added to the phase encoding gradient waveform. As is well known in the art, each SSFP pulse sequence acquires a single k-space view of the subject and the pulse sequence is repeated and the amplitude of the phase encoding gradient 204 and its equal, but opposite rewinder 218 are stepped through a series of values to sample 2D k-space in a prescribed manner.

It should be apparent to those skilled in the art that many other SSFP pulse sequences may be used. For example, SSFP pulse sequences which radially sample k-space during each view or which sample a spiral sampling trajectory during each view may be employed.

Figure 7:
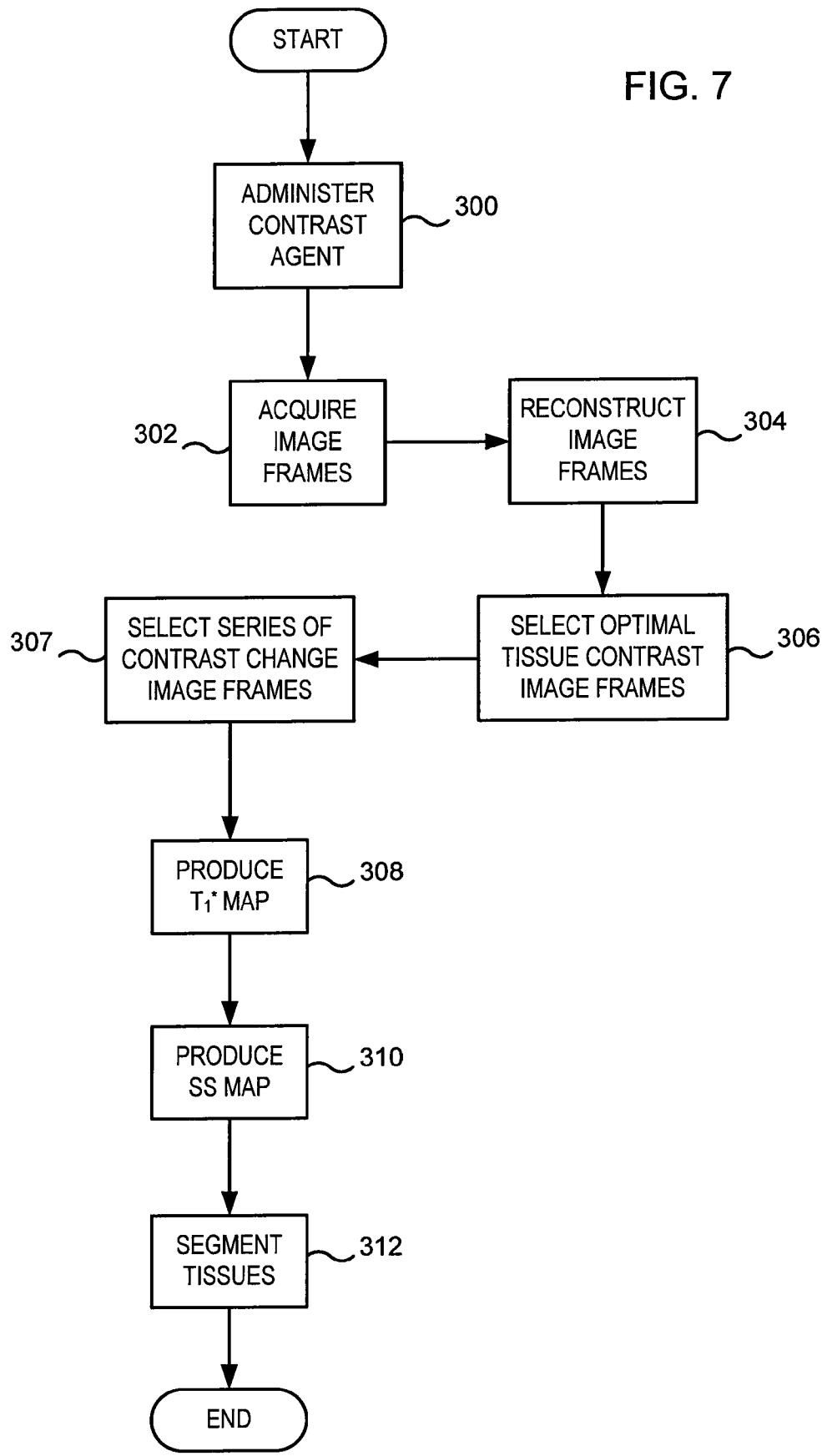
FIG. 7 is a flow chart of the steps performed using the preferred embodiment of the invention.

Referring still to FIG. 2 and to FIG. 7, when the scan is initiated the subject is injected with a contrast agent as indicated at process block 300 and a period of 10 to 30 minutes is allowed to pass before MRI data is acquired. The data acquisition process is then performed using the above described pulse sequence as indicated at process block 302. During the first cardiac cycle of the scan the inversion pulse 152 is produced at a preselected time after the gating signal 150 and then the RF excitation pulses 200 used in the SSFP pulse sequence are produced to establish a spin magnetization equilibrium. No MRI data is acquired during the first cardiac cycle. During the subsequent R-R intervals, the inversion pulse 152 is produced after the preselected delay and the SSFP pulse sequences are performed in their entirety to acquire MRI data. The inversion pulse 152 is set to a delay (TDEL) such that the image frames that show the best contrast between viable and nonviable myocardium occur in mid-diastole, while ensuring that systolic images are acquired when the image contrast is no longer changing substantially.

The scan continues for a sufficient number of heart beats to acquire a k-space image data set at each cardiac phase segment 154 from which a two-dimensional image frame may be reconstructed. It should be apparent that the number of segments that are acquired and the number of SSFP repetitions performed during each segment 154 is a matter of choice. Longer segments 154 enable more SSFP repetitions during each segment so that total scan time (i.e., number of heart beats) is reduced. However, this reduces the number of image frames that are produced during each cardiac cycle and it increases cardiac motion artifacts. Typically 8 to 16 pulse sequences are performed during each segment 154 and this enables the scan to be completed in one breath hold.

Between 10 and 15 short-axis 2D images are obtained to cover the entire left ventricle of the heart. Scan parameters in one preferred embodiment are:
bandwidth=+125 kHz
RF pulse flip angle=30 degrees
views per segment=16
pulse sequence TR=2.7 ms
pulse sequence TE=1.3 ms
FOV=320 mm
slice thickness=8 mm
imaging matrix=192×192
NEX=1
TDEL=500 ms This embodiment requires 13 heartbeats to complete the scan (one to establish steady state and 12 to acquire MRI data). This requires an average breath-hold by the subject of 11 seconds.

This preferred embodiment yielded twenty image frames that are reconstructed from the k-space data sets acquired during each segment 154 as indicated in FIG. 7 indicated at process block 304. In the preferred embodiment this is a 2DFT reconstruction. The heart wall motion and thickness can be seen in all of these image frames enabling wall motion abnormalities to be seen and cardiac function values to be computed. Each segment 152 has a temporal window of approximately 50 ms, allowing even small wall motion abnormalities to be detected.

It should be apparent to those skilled in the art that many different image reconstruction methods may be used depending on the type of SSFP pulse sequence employed and the data acquisition method used. For example, k-space data acquired with spiral and radial sampling trajectories are regridded to a Cartesian grid prior to performing a 2DFT reconstruction. Also, if parallel imaging such as SENSE, SMASH or GRAPPA is used to reduce the amount of k-space data needed to reconstruct each image frame, the reconstruction method applicable to such technique is used. And, of course, 3D spatial encoding can be used to acquire and reconstruct three-dimensional images.

As indicated at process block 306, the physician can select from the reconstructed image frames those which depict optimal tissue contrast. Because the present method acquires image frames in succession after the RF inversion pulse 152, the physician can select the particular images that provide the optimal tissue contrast characteristics during their respective $T_1$ recoveries. This eliminates the requirement of conventional DE-MRI methods in which the optimal TI interval needed to null myocardium signal is done by a lengthy trial-and-error process involving two to four additional scans at different preset TI intervals. The optimum TI varies from patient to patient, and it can also vary over the 5-10 minutes during which a stack of short-axis images is acquired, leading to reduced contrast in some of the conventional DE MRI images.

Using the present method the physician is presented after a single scan with a series of image frames having different tissue contrast characteristics to choose from. It has been found that due to the improved visualization of the infarct-blood boundary, small subendocardial infarcts can be more easily identified and infarct transmurality can be more easily assessed when the present invention is used.

Another advantage of the present invention is that the recovery of different tissue types can be calculated and observed in the succession of acquired image frames. To accomplish this, a set of image frames are selected as indicated at process block 307 which depict the signal recovery of tissues in the heart at successive times after the inversion pulse 152. The selections are made not only to sample signal recovery at a number of different times, but also to minimize motion which misregisters tissue voxels. Since the heart is beating, a certain amount of misregistration will result and an image frame registration procedure such as that described in U.S. Pat. No. 6,292,683 entitled "Method and Apparatus for Tracking Motion in MR Images" can be used to align tissues depicted in the series of selected image frames at the same location in each image frame. The description in this patent which issued on Sep. 18, 2001 is incorporated herein by reference, but many different image registration methods are known in the art.

From this information it is possible to produce a $T_1^*$ map of the imaged tissues as indicated at process block 308. For each image pixel the magnitude of the MR signal (signal=ss $(1-e^{-TR/T_1^*})$) is plotted as a function of recovery time for the successive segments 154. A $T_1^*$ recovery curve is fitted to these points using a method described by Schmitt, P, Griswold M A, Jakob P M, Kotas M, Gulani V, Flentje M, Haase A., "Inversion recovery TrueFISP: quantification of $T_1$, $T_2$ and spin density", *Magn Reson Med* 2004; 51: 661-667. The $T_1^*$ of the tissue is determined from this curve and the calculated $T_1^*$ of each pixel determines the brightness of the corresponding pixel in the $T_1^*$ map. $T_1^*$ maps generated from a set of acquired image frames provide a method for determining infarct heterogeneity by comparing the $T_1^*$ values of the peri-infarct region with those of healthy myocardium and the infarct core. Once generated, these $T_1^*$ maps may also be helpful in assessing a wide range of cardiomyopathies.

As indicated at process block 310 the steady state (ss) value of the signal at each image pixel can also be determined from these $T_1^*$ recovery curves. The steady state value ss is the maximum signal value which occurs when the longitudinal spin magnetization is fully recovered after the inversion pulse. Both the $T_1^*$ and the ss parameters of tissues are useful in segmenting tissues.

The last step indicated at process block 312 is to segment the various tissue types using the $T_1^*$ and ss maps. A fuzzy clustering method such as that described by D. E. Gustafson and W. C. Kessel, "Fuzzy clustering with a fuzzy covariance matrix," in Proc. IEEE Conf. Decision Contr., San Diego, Calif., 1979, pp. 761-766 is used in the preferred embodiment. A scatter plot, which has the $T_1^*$ versus ss value of every image frame pixel is fed into the fuzzy clustering process and the pixels are automatically separated into three clusters. The pixels can then be color coded on a displayed image frame according to the tissue type which it has been classified—infarcted myocardium, normal myocardium or blood. From the probability values produced by the fuzzy clustering process it is also possible to segment pixels made up of a mixture of infarcted myocardium and normal myocardium. The number of pixels in this resulting "gray zone" indicated by this mixture of two tissue types has been shown to predict which subjects are more likely to suffer cardiac arrhythmias.

The invention claimed is:

1. A method for producing a series of cardiac gated magnetic resonance images of a subject's heart, the steps comprising:
   a) administering a contrast agent to the subject;
   b) producing a gating signal that indicates the start of the subject's cardiac cycle;
   c) producing a radio frequency (RF) inversion pulse that inverts spin magnetization throughout a field of view a preset time after the gating signal is produced;
   d) acquiring k-space data as a series of data segments at successive cardiac phases after the RF inversion pulse is produced using a plurality of steady-state free precession (SSFP) pulse sequences during a time period in which the inverted spin magnetization recovers such that some data segments in the series of data segments are acquired when tissue contrast is changing and other data segments in the series of data segments are acquired when tissue contrast is no longer substantially changing;
   e) repeating steps b) through d) until a desired amount of k-space data is acquired in each data segment;
   f) reconstructing a series of image frames depicting the heart at a succession of cardiac phases using the k-space data acquired in the series of data segments, and in which images in the series of image frames reconstructed from the data segments acquired when tissue contrast is changing depict a time-varying tissue contrast of the heart, and in which images in the series of image frames reconstructed from the data segments acquired when tissue contrast is no longer substantially changing depict cardiac wall motion; and
   g) producing a $T_1^*$ map by:
      i) determining for a given pixel location in the $T_1^*$ map, a $T_1^*$ value by fitting magnitude values from corresponding pixel locations in the series of image frames reconstructed in step f) to a signal model that relates magnitude values to $T_1^*$; and
      ii) setting magnitude values for each given pixel location in the $T_1^*$ map to the corresponding $T_1^*$ value determined in step g)i).

2. The method as recited in claim 1 which further includes:
   h) performing a magnetization equalization pulse sequence during a cardiac cycle preceding the performance of step c), the magnetization equalization pulse sequence including performing an RF inversion pulse that inverts spin magnetization throughout the field of view the preset time after the gating signal is produced followed by an SSFP pulse sequence in which no k-space data is acquired.

3. The method as recited in claim 1 in which the preset time interval in step c) is selected such that images that depict optimal contrast between viable and nonviable myocardium tissues of the heart are acquired during mid-diastole of each cardiac cycle.

4. The method as recited in claim 1 in which the desired amount of k-space data in each data segment is acquired in step e) by performing a number of SSFP pulse sequences during a single breath hold of the subject.

5. A method for producing a series of delayed contrast enhanced magnetic resonance images of a subject's heart, the steps comprising:
   a) producing a gating signal that indicates the start of the subject's cardiac cycle;
   b) producing a radio frequency (RF) inversion pulse that inverts spin magnetization throughout a field of view a preset time after the gating signal is produced;

c) acquiring k-space data as a series of data segments at successive cardiac phases after the RF inversion pulse is produced using a plurality of steady-state free precession (SSFP) pulse sequences during a time period in which the inverted spin magnetization recovers such that some data segments in the series of data segments are acquired when tissue contrast is changing and other data segments in the series of data segments are acquired when tissue contrast is no longer substantially changing;

d) repeating steps a) through c) until a desired amount of k-space data is acquired in each data segment;

e) reconstructing a series of image frames depicting the heart at a succession of cardiac phases using the k-space data acquired in the series of data segments, and in which images in the series of image frames reconstructed from the data segments acquired when tissue contrast is changing depict a time-varying tissue contrast of the heart, and in which images in the series of image frames reconstructed from the data segments acquired when tissue contrast is no longer substantially changing depict cardiac wall motion; and f) producing a $T_1^*$ map by:
  i) determining for a given pixel location in the $T_1^*$ map, a $T_1^*$ value by fitting magnitude values from corresponding pixel locations in the series of image frames reconstructed in step e) to a signal model that relates magnitude values to $T_1^*$; and
  ii) setting magnitude values for each given pixel location in the $T_1^*$ map to the corresponding $T_1^*$ value determined in step f)i).

6. The method as recited in claim 5 which includes:
g) performing a magnetization equalization pulse sequence during a cardiac cycle preceding the performance of step b), the magnetization equalization pulse sequence including performing an RF inversion pulse that inverts spin magnetization throughout the field of view the preset time after the gating signal is produced followed by an SSFP pulse sequence in which no k-space data is acquired.

7. The method as recited in claim 5 in which the preset time interval in step b) is selected such that images that depict best contrast between viable and nonviable myocardium tissues of the heart are acquired during the mid-diastole of each cardiac cycle.

8. The method as recited in claim 5 in which the desired amount of k-space data in each data segment is acquired in step d) by performing a number of SSFP pulse sequences during a single breath hold of the subject.

9. A method for determining a health of a subject's heart, the steps comprising:
a) acquiring a series of image frames of the subject's heart with a magnetic resonance imaging (MRI) system by performing a scan which includes:
a)i) administering a contrast agent to the subject;
a)ii) performing a cardiac gated, segmented acquisition during each of a series of cardiac cycles and after the application of an inversion radio frequency (RF) pulse during each cardiac cycle to acquire a corresponding series of image frame data sets having tissue contrast that differs as a function of inversion recovery time (TI) after the inversion RF pulse; and
a)iii) reconstructing a series of image frames from the corresponding image frame data sets;
b) producing a $T_1^*$ map indicating the inversion recovery time of tissues depicted in the image frames; and
c) producing a steady state map indicating fully recovered signal values of tissues depicted in the image frames.

10. The method as recited in claim 9 in which step a)ii) is performed using a steady state free precession (SSFP) pulse sequence to direct the MRI system.

11. The method as recited in claim 9 which further includes:
d) selecting from the series of image frames, one or more image frames that depicts optimal contrast between infarcted myocardium tissue and normal myocardium tissue.

12. The method as recited in claim 9 which further includes:
e) producing a segmented image frame by using the $T_1^*$ map and the steady state map as input to a fuzzy clustering process.

13. The method as recited in claim 12 in which the segmented image frame is segmented to indicate normal myocardial tissues, infarcted myocardial tissues, and blood.

14. The method as recited in claim 13 in which the normal myocardial tissues, infarcted myocardial tissues, and blood are indicated in the segmented image frame by color coding pixels in the segmented image frame.

15. The method as recited in claim 9 in which step b) includes producing the $T_1^*$ map by:
b)i) selecting a set of image frames from the reconstructed series of image frames that depict recovery of signals at each pixel location therein over a period of time following the inversion RF pulse;
b)ii) fitting recovery curves to the signals at corresponding pixel locations in the selected set of image frames; and
b)iii) calculating a $T_1^*$ value for each pixel location in the $T_1^*$ map from the recovery curve for a corresponding pixel location in the set of image frames.

16. The method as recited in claim 15 in which step c) includes producing the steady state map by calculating a steady state value for each pixel location in the steady state map from the recovery curve for a corresponding pixel location in the set of image frames.

17. The method as recited in claim 15 in which step b)i) further includes registering the selected set of image frames to align tissues depicted in the selected set of image frames at substantially same pixel locations in each of the image frames in the selected set of image frames.

* * * * *